United States Patent [19]

Keller

[11] Patent Number: 4,981,241
[45] Date of Patent: Jan. 1, 1991

[54] DOUBLE DELIVERY CARTRIDGE FOR TWO COMPONENT MASSES

[76] Inventor: Wilhelm A. Keller, Riedstrasse 1 CH-6330, Cham, Switzerland

[21] Appl. No.: 524,691

[22] Filed: Apr. 30, 1990

Related U.S. Application Data

[63] Continuation of Ser. No. 202,186, Jun. 2, 1988, abandoned.

[30] Foreign Application Priority Data

Jun. 10, 1987 [CH] Switzerland .......................... 2176/87

[51] Int. Cl.⁵ .............................................. B67D 5/42
[52] U.S. Cl. .................................. 222/137; 222/145; 222/566
[58] Field of Search ................ 222/94, 135, 136, 137, 222/145, 326, 327, 391, 566, 567, 570

[56] References Cited

U.S. PATENT DOCUMENTS

| | | | |
|---|---|---|---|
| 1,709,445 | 4/1929 | Tomes | 222/327 X |
| 3,117,696 | 1/1964 | Herman et al. | 222/137 |
| 3,231,156 | 1/1966 | Schultz | 222/570 X |
| 3,323,682 | 6/1967 | Creighton, Jr. et al. | 222/94 |
| 3,330,444 | 7/1967 | Raypholtz | 222/137 |
| 3,390,814 | 7/1968 | Creighton, Jr. et al. | 222/145 X |
| 3,570,719 | 3/1971 | Schiff | 222/137 |
| 3,827,602 | 8/1974 | Nicholls | 222/137 |
| 3,828,980 | 8/1974 | Creighton et al. | 222/137 |
| 4,260,077 | 4/1981 | Schroeder | 222/137 |
| 4,392,589 | 7/1983 | Herold | 222/137 |
| 4,471,888 | 9/1984 | Herb et al. | 222/137 |
| 4,631,055 | 12/1986 | Redl et al. | 222/135 X |
| 4,676,410 | 6/1987 | von Flue | 222/137 X |
| 4,690,306 | 9/1987 | Staheli | 222/137 X |
| 4,753,536 | 6/1988 | Spehar et al. | 222/137 X |
| 4,771,919 | 9/1988 | Ernst | 222/94 X |
| 4,869,400 | 9/1989 | Jacobs | 222/137 |
| 4,871,090 | 10/1989 | Hoffmann | 222/137 X |

FOREIGN PATENT DOCUMENTS

| | | |
|---|---|---|
| 0236129 | 9/1987 | European Pat. Off. . |
| 3420323 | 12/1985 | Fed. Rep. of Germany . |
| 3501331 | 7/1986 | Fed. Rep. of Germany . |
| 2399861 | 3/1979 | France . |
| 2188373 | 9/1987 | United Kingdom ................ 222/137 |

*Primary Examiner*—Kevin P. Shaver
*Attorney, Agent, or Firm*—Darby & Darby

[57] ABSTRACT

For a dual dispenser cartridge, the front end orifices of both storage cylinders, arranged with parallel axes, are each surrounded by a circular stud. A transition member, positioned ahead of the front ends, provides the connection between two separate discharge channels and the aforementioned orifices by means of a permanent, axial push-fit connection, the channels terminating within a common orifice. The transition member may be interlocked with each of the cylinders by means of a snap lock connection and defines together with them a rigid, ready-to-use unit. Both cylinders may be manufactured in one piece, comprising double wall separations, and interlocking webs; separately manufactured cylinders with plug-in or snap-lock connection are also feasible. The cylinder spacing of all dual cartridges can be made equal to the spacing of the rams of a dispensing device. An identical transition member may be used.

16 Claims, 2 Drawing Sheets

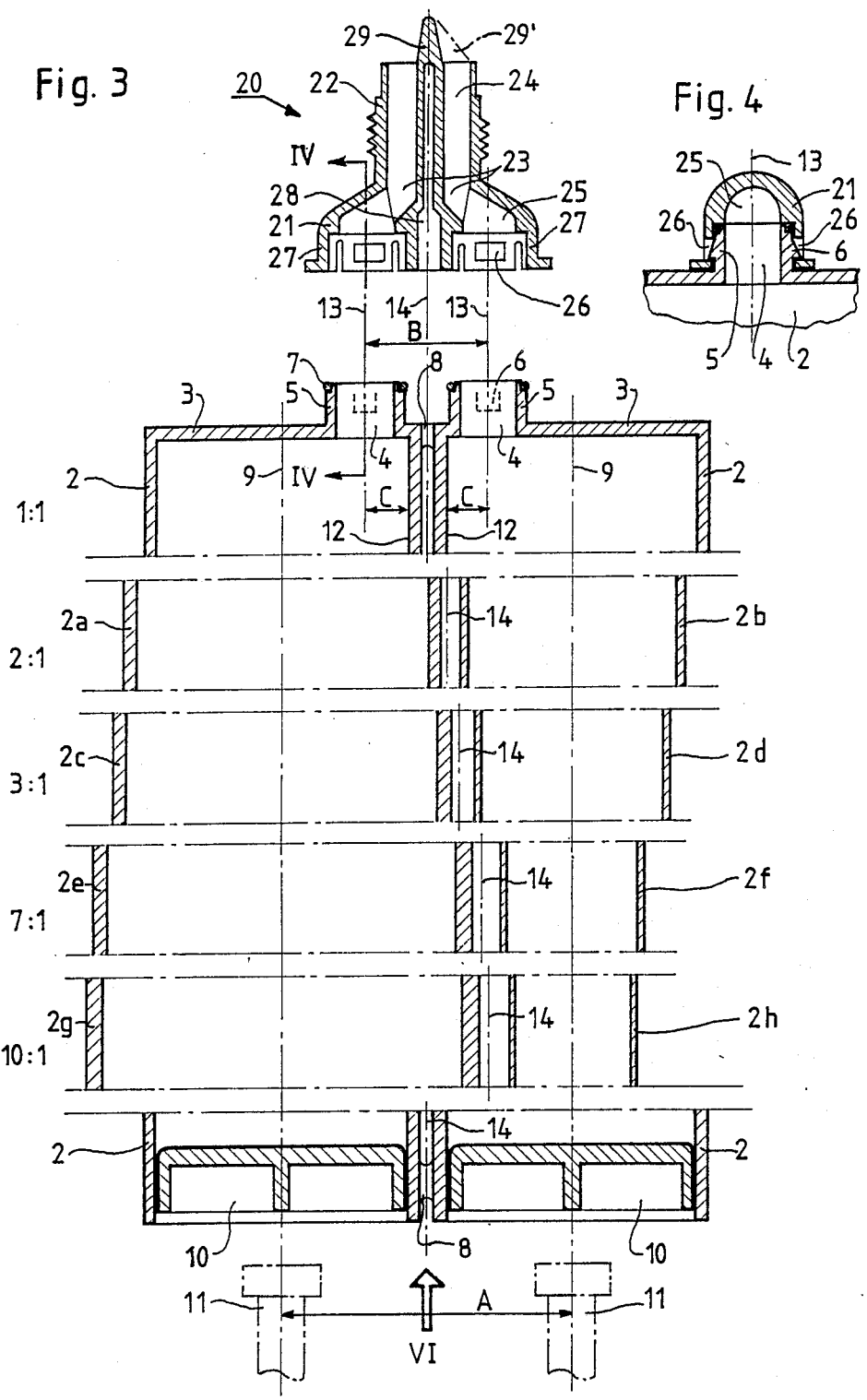

DOUBLE DELIVERY CARTRIDGE FOR TWO COMPONENT MASSES

This is a continuation of application Ser. No. 202,186, filed June 2, 1988 now abandoned.

The invention relates to a dual dispenser cartridge for two-component compounds, having two interlocked storage cylinders, separated by double walls, arranged axially parallel side-by-side, and each comprising one front end discharge opening, wherein both discharge openings are located next to each other on the common center line of both storage cylinders.

BACKGROUND OF THE INVENTION

Two-component systems, e.g., for adhesives, sealing compounds, dental impression compounds etc., are composed of two different substances belonging together and stored in a known manner, within two separate storage cylinders for distribution purposes. For processing, both substances are mixed at a predetermined ratio, resulting in a chemical reaction causing their hardening or solidification. Extrusion of both components from the cylinders is effected by simultaneous actuation of feeder pistons, one of which is located within each cylinder, thereby pressing out the substances through the front side discharge openings.

A previously known dual dispenser cartridge of the above described variety (U.S. Pat. No. 4,260,077) comprises a nozzle for each of the two discharge openings, such that two independent strings of substances are being pressed out, requiring subsequent manual mixing thereof. Such a process, however, is inefficient and does not guarantee uniform blending, as is essential for obtaining perfect results. For conveniently achieving thorough mixing of the components, it is therefore common practice to press these through a mixer tube attached to the cartridge cylinders (so called static or flow mixer).

When attaching two-component cartridges to a mixer tube, it is known practice to use special transition members, which may be part of a cartridge dispensing device (e.g., DE-OS No. 35 01 331), or which may be independent thereof (DE-OS No. 34 20 323, FIG. 4 and EP-A No. 0 236 129, FIG. 2). Such configurations, however, involve various, significant disadvantages:

Only single cartridges can be used, so that in use erroneous combinations cannot be excluded (combination of components which do not match or combination of two identical components);

Joining of individual cartridges, transition member and mixer tube, can only be accomplished immediately before the application, resulting in troublesome preparations for each new cartridge;

Individual cartridges are equipped with a front end threaded stud, each of which is to be screwed into one of the internal threads of the transition member. Interlocking of individual cartridges, therefore, is not possible, and as a consequence, this arrangement shows poor mechanical stability, and furthermore, the threaded studs must be concentric, i.e., coaxial with respect to the cylinder axis;

This last mentioned circumstance leads to a large distance between both entry positions (inside thread) of the transition member, thus resulting in extended, convoluted conduction channels from there to the mixer entry, such channels being difficult to manufacture and including a considerable amount of dead volume. Such transition members, therefore, could hardly be manufactured as inexpensive disposable components, thus, resulting again in cleaning problems, etc.

Another known arrangement (FR-A No. 2 399 861) is also based on individual cartridges. A sort of tri-sectional tube serves as a transition member, whereby one section comprises an integrated mixing arrangement and the two other sections are to be pushed onto discharge studs at the cartridges. Such a component, if at all suitable for manufacturing, could hardly be manufactured other than as a rubber-like flexible tube. Such, however, cannot provide a connection of stable shape between the individual cartridges, and the connection to the studs cannot sustain the high pressure developing when pressing out the components.

It is an object of the present invention to eliminate the aforementioned drawbacks of existing products and to provide a readily usable dual cartridge, which permits proper distribution and storage of both associated components already from the processing plant or the filling facility, whereby the mixer tube can be readily attached without difficulties.

SUMMARY OF THE INVENTION

The dual dispenser cartridge of the present invention is characterized in that a transition member is provided, positioned ahead of the front end of the storage cylinders, comprising for both components a common orifice for attachment of a mixer tube, and also comprising two discharge channels, extending separately to the extremity of the orifice, said transition member being affixed to both storage cylinders by means of a permanent axial push-fit connection which connects both discharge channels to the discharge openings of the storage cylinders, defining a rigid unit in conjunction with both storage cylinders. Thanks to this design concept, based on adjoining (normally eccentrically arranged) discharge openings, and based on a permanent push-fit connection, manufacture of the transition member as well as the cylinders as cheap disposable units will hardly cause any problems. In particular, the constituent parts lend themselves to a very desirable, comprehensive standardization with regard to dual dispenser cartridges with various cross section ratios of their cylinders, such as are needed for different mixing ratios of the components.

Various resulting suitable design arrangements incorporating the subject of the invention, are possible; in particular, manufacturing of the two associated storage cylinders can be accomplished, either (joined) in one piece, or separately, whereby different materials may be selected for each cylinder of a pair, either for reasons of mechanical strength or compatibility with the contents to be filled in.

Based on dual dispenser cartridges the invention also includes a series of such dual dispenser cartridges having equally spaced cylinder axes and equal total rated volume, however, of variable cross section ratios of their respective cylinder pairs; the so defined series is especially suitable for service with always the same dispensing device, having a fixed axial distance of the extrusion rams corresponding to the axial distance of the cylinders.

The following, practical embodiments of the invention are described in more detail, in conjunction with the drawing.

BRIEF DESCRIPTION OF THE DRAWINGS

FIG. 3 shows a longitudinal section of the dual dispenser cartridge according to FIG. 1 before engaging the push-fit connection between the storage cylinders and the transition member, whereby several cylinder pairs with variable cross section ratios and belonging to a series are also indicated;

FIG. 4 shows a section along the line IV—IV in FIG. 3, with the transition member attached;

DESCRIPTION OF THE PREFERRED EMBODIMENTS

Figure 1:
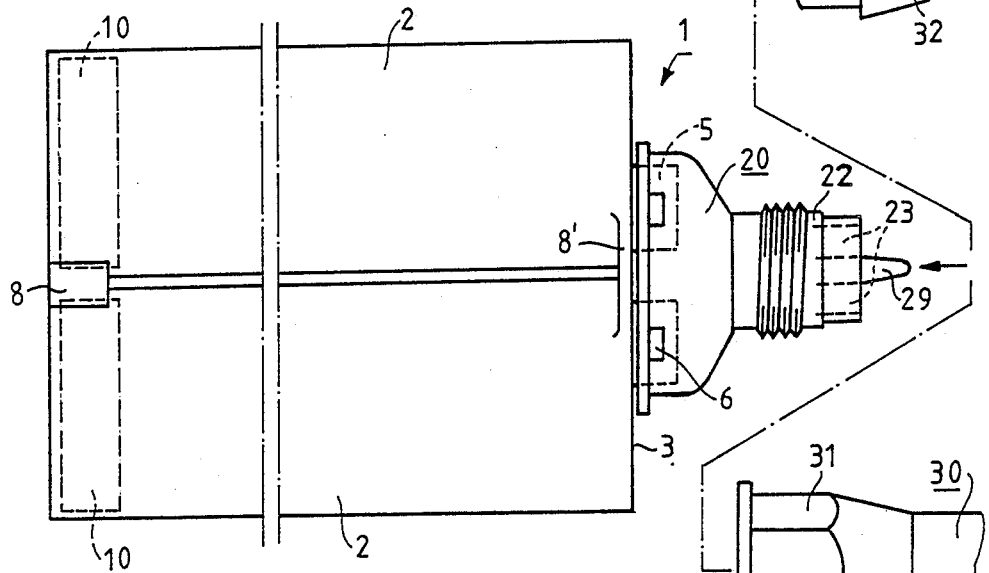
FIG. 1 is a side view of a dual cartridge unit, comprising a pair of storage cylinders to which a transition member is permanently attached; furthermore, there is shown an attachable mixer tube and an optionally insertable stopper.

The dual dispenser cartridge 1 for two-component substances, as shown in FIGS. 1 to 6, is composed of two storage cylinders 2 in axially parallel, side-by-side arrangement, separated by double walls, and a transition member 20, positioned ahead of the two storage cylinders. A feeder piston 10 is introduced into the rear end of each cylinder (FIG. 1, left and FIG. 3, bottom). The two storage cylinders 2 are intended for receiving each one mass or component of a so called two-component system. For use the dispenser cartridge is placed in a known manner into a dispensing device which comprises two parallel rams 11, shown at the bottom of FIG. 3 with dash-dotted lines. Whenever operating the herein not shown dispensing device, its rams 11 are moved synchronously against the feeder pistons 10, and through the advancement of the feeder pistons within the storage cylinders, the cylinder contents are dispensed through each of the respective discharge openings 4 located at the front end.

Figure 2:
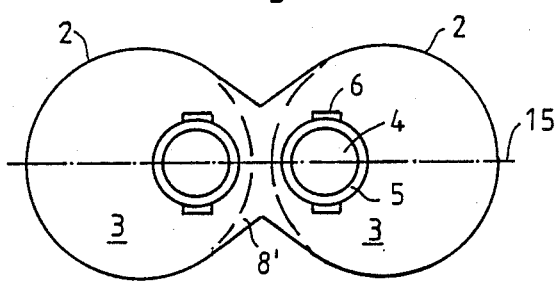
FIG. 2 is a front end view of the dual cartridge according to FIG. 1 without transition member.
Figure 5:
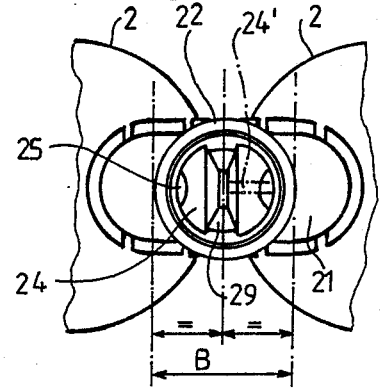
FIG. 5 is a partial front end view of the dual cartridge and transition member according to FIG. 3.
Figure 6:
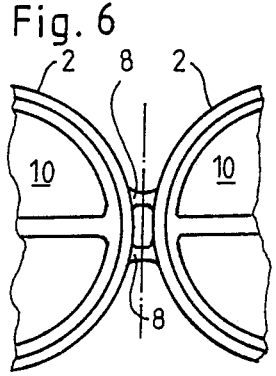
FIG. 6 is a partial rear end view of the twin cartridges in the direction of the arrow VI in FIG. 3.

As can be seen in FIG. 2, the front end discharge openings 4, of the two interlocked storage cylinders 2 are located adjacently (eccentrically with respect to the corresponding cylinder axis) on the common center line 15. According to FIG. 1, both cylinders 2 and the transition member 20 are interlocked as a rigid unit 1 by means of a permanent, axial push-fit connection, as described in more detail below. The push-fit connection also provides a leak-proof connection between the discharge openings 4 and two associated discharge channels 23, extending separately within the transition member 20 to the end of the orifice 22. The orifice 22, which according to FIG. 5 is of circular shape, therefore is common to both components. During processing the cartridge contents, orifice 22 serves to attach a mixer tube 30, preferably a static type mixer (broken away depiction of FIG. 1). Attachment to the external thread of the orifice 22 is effected in a known manner by means of an integral threaded sleeve 31 on the tube 30, or by means of a screw cap. A separation wall 29, protruding beyond the orifice 22, keeps the two components separated within the mixer tube 30 until reaching the first mixing element (not shown).

During storage and distribution of the filled dual cartridge 1, the orifice can be closed off by means of a stopping plug 32 comprising stoppers 33 protruding into the channels 23; the stopping plug can be fastened by means of the aforementioned screw cap (not shown). Another closing off method includes the attachment of so called rupture foils or disks behind the discharge openings 4, which will become ruptured by the internal pressure within the cylinders 2 at the beginning of substance discharge.

Both storage cylinders 2 of the present example are fabricated as one unit from injection-molded plastic, such that they are separated by double walls. Connection of both cylinders can be effected, for example, by means of two connecting webs 8 within the rear (FIG. 6) and front ends (FIG. 3) of the cylinders; in place of the front end connecting webs it is also feasible to provide a connecting bridge 8', flush with the front wall 3 according to FIGS. 1 and 2.

The discharge opening 4 in each cylinder front end 3 consists of a circular bore, of which the axis 13 is preferably for both cylinders of equal distance C with respect to the cylinder inner wall 12. Each of the two discharge openings 4 is surrounded by a circular, preferably cylindrical, stud 5 originating from the respective front wall 3.

The transition member 20 associated to the pair of cylinders 2 also consists of an injection-molded plastic component. It includes a connecting region 21 facing the cylinders, and the aforementioned orifice 22. The connecting region 21 includes two preformed, essentially cylindrical sleeves 27 closely fitting over the two studs 5. The shape of the separated discharge channels 23, contained within the transition member 20, is clearly seen in FIGS. 3 and 5. Mainly for reasons of injection molding techniques, each discharge channel 23 preferably consists of two longitudinal sections 24 and 25, which are offset with respect to each other in an axially parallel arrangement, however overlapping within their cross sections. Like the two cylinders 2, the channels 23 are also separated by a cavity 28 between double walls, preferably along their entire length, i.e., up to the end of the orifice 22. Separation by double walls assures that, even for long term storage, no diffusion or premature chemical reaction takes place between the two filled-in components.

For the transition member 20, the connecting region 21 is preferably arranged symmetrically to the axis 14 of the common orifice 22. With equal distance C of the axes 13 of the studs 5 from the respective inside wall 12 of the cylinder, the axis 14 falls within the center between these two inside walls (FIG. 3).

In case of a dual dispenser cartridge with equal cross sections of the two cylinders 2, discharge openings 4 as well as discharge channels 23 within the transition member, are made of identical cross sections. However, in case of volume mixing ratios different from 1:1 for the two components, and different cylinder cross sections of the pair of cylinders, the openings 4 as well as the adjoining longitudinal sections 25 may still be made equal (and symmetrical to the axis 14); it is useful, however, to dimension the discharge cross sections of the two discharge channels 23 within the common orifice 22, with the same proportions as the cross sections of the two storage cylinders; FIG. 5 indicates, on the right hand side, in dash-dotted lines a respectively constricted front end section of channel 24' (as compared to the channel section 24 on the left hand side of the figure). As schematically shown in FIG. 3 at 29', the wall 29 too must be made to conform with requirements for the connection to the mixer. For unequal mixing ratios, this cross section adjustment at the opening of the discharge channels 23 causes the two components to enter the mixer in correspondingly different ratios of volume, however, in strings of equal length and equal speed.

The permanent, axial push-fit connection between the transition member 20 and the two storage cylinders 2, according to FIGS. 3 and 4, can be accomplished by means of a snap lock: For example, at the outside of each stud 5, located opposite to each other, there are two integral wedge-shaped noses 6. At corresponding locations of the connecting sleeves 27, a rectangular "window" 26 is provided at the transition member; as shown, the wall of the sleeve may have cut-outs on both sides of each window 26, such that the corresponding section of the wall can be slightly bent outward. Whenever the connecting region 21 is pushed over the two studs 5, the noses 6 snap into the window 26, thus providing a solid interlock between the two storage cylinders and the transition member.

According to FIGS. 3 and 4, each stud 5 is sealed with respect to the connecting region 21 by means of a sealing ring 7; the sealing ring 7 can be arranged within the front end region as shown, or within a circular groove on the stud 5. In place of a sealing ring 7, a lip seal could also be arranged between each stud 5 and the connecting region 21 (not shown).

The push-fit connection between the cylinders and the transition member could of course be conceived in various other snap lock connection designs; the push-fit connection can also be secured by bonding or welding. In every case, however, the push-fit connection is a permanent one, i.e., it is not meant for subsequent disassembling; the unit 1, assembled from components 2 and 20, defines a unified disposable part. A snap lock connection of the type as described, or the aforementioned "secured" push-fit connection (contrary to a screw-on connection), cannot either be disassembled by turning the cylinders. As essential contribution to shape rigidity of the unit 1 is obtained by the fact that cylinders 2 are directly, mutually interlocked.

Figure 7:
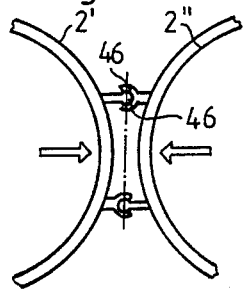
FIG. 7 shows as an end view a sample of a spacing snap lock for both storage cylinders when individually manufactured.

It can be useful to separately fabricate the two storage cylinders belonging to one pair, and to assemble them afterwards. Particularly in this case, they can be manufactured from different materials, for instance for reasons of sturdiness or in consideration of stability or compatibility with the components to be filled in. Separately manufactured cylinders should be mutually interlocked by means of a spacing connection, at least within the area of their rear ends. A similar joint may also be arranged within the area of the cylinder front end, it is, however, feasible that the cylinder front sections are interlocked exclusively by means of the transition member 20. Preferably located at their front ends, the cylinders shall have incorporated provisions against longitudinal displacement, e.g., by means of interlocking tongues. An example of a suitable spacing type snap connection is shown in FIG. 7: Two identical, symmetrical profiles 46 have been arranged at two separately manufactured cylinders 2' and 2", which can be radially inserted within each other, in direction of the arrows, to create a stable snap connection. Furthermore, a push-on type, spectacle frame shaped spacing configuration, fitting axially over the cylinders, is also conceivable.

The construction of dual dispenser cartridges with a transition member arranged ahead of the front end, as described, lends itself to relatively simple, efficient production and assembly methods. This unit shows high stability during its use and guarantees perfect sealing and proper separation of the two components, even for extended periods of storage. The mixer tube can easily be attached to the common orifice of the ready-to-use unit.

This construction especially permits concepts of highly standardized series of several dual dispenser cartridges of equal total rated volume, whereby, from one dual cartridge to another, the ratio of cross sections of the pair of cylinders is variable. Thus, it is possible to conceive dual cartridges for application/mixing ratios of the components, for example of 1:1, 2:1, etc., up to for example 10:1, or according to requirements, also for fractional ratios. FIG. 3 shows corresponding cylinder diameters of cylinder pairs $2a$, $2b$; $2c$, $2d$; $2e$, $2f$; $2g$, $2h$ for such a series (for a given total rated volume of both cylinders and under the assumption of equal cylinder length), with cross section/mixing ratios differing from 1:1. As can be seen, wall thickness too can be adjusted according to the various cylinder diameters, to conform with requirements of stability. An outstanding characteristic of such a series is given by the fact that for all cylinder pairs of the series, the distance A between cylinder axes is equal and corresponds to the given spacing of the rams 11 of an associated dispensing device. Thanks to this characteristic, it is possible to use all cartridges of a series with the same dispensing device, whereby the forces exerted by the rams are always applied concentrically against the corresponding delivery pistons 10.

In the layout of a series, it is furthermore possible to maintain equal distance B between the axes 13 of the two studs, and thus to use always essentially equal transition members 20. As indicated in FIG. 3, only the position of the axis of symmetry 14 is moved between the axes 9 of the cylinders as a function of diameter or cross section ratios of the corresponding pair of cylinders. Generally the conditions are such, that with a given axial distance B between the studs and axial distance A between the cylinders, the studs 5 of both storage cylinders thereof are positioned eccentrically with respect to the cylinder axis 9; in an extreme case, however, (for considerable differences in cylinder diameter within the pair), it may be of advantage to let the axis 13 of the stud on the smaller cylinder coincide with the axis 9 of the cylinder, and to arrange only the stud on the large cylinder in a correspondingly eccentric position.

An important advantage of the herein described dual cartridge, according to the invention, must be seen in its consequential avoidance of environmental contamination: With heretofore known systems, as mentioned in the beginning, comprising individual cartridges which are detachably interlocked with a (reusable) transition member and which will be separated after use, it is possible that unused portions of reactive, and possibly poisonous materials can escape. Contrary to this, the dual cartridge, according to the invention, will be disposed of together with the transition member and the attached mixer tube as a completely and tightly sealed unit, i.e., at the front end sealed by the polymerized mixture of the components within the mixer tube, and rearwardly sealed by the delivery pistons. Thus, no leftover reactive components, endangering the environment, are allowed to escape.

I claim:

1. A dual dispenser cartridge assembly for two-component compounds, comprising:
   two interlocked storage cylinders, separated by double walls, arranged axially parallel side-by-side, and each cylinder having one front end discharge opening, wherein both discharge openings are located next to each other centered on a common diametral plane through both storage cylinders, the distance between the axes of the discharge openings being less than the distance between the cylinder axes, said dual dispensing cartridge assembly being subject to long term storage and subsequent dispensing of said components;
   a transition member positioned ahead of the front end of the storage cylinders, said transition member having for both components a mounting for attachment of a mixer tube, and two discharge channels, extending separately to the extremity of the mounting, said transition member being undetachably integral with both storage cylinders and connecting both said discharge channels to said discharge openings of the storage cylinders, said transition member defining a rigid unit in conjunction with both said storage cylinders; and
   means for rendering said transition member undetachably integral with said cylinders.

2. Dual dispenser cartridge assembly as defined in claim 1, wherein the transition member is manufactured as a separate injection-molded component, and said means for rendering comprises a snap lock connection.

3. Dual dispenser cartridge assembly as defined in claim 1, wherein the two discharge channels within the transition member are separated by double walls along their entire length.

4. Dual dispenser cartridge assembly as defined in claim 1, wherein each of the discharge openings is defined by a respective circular stud, and the transition member comprises a region which sealingly overlaps the two studs.

5. Dual dispenser cartridge assembly as defined in claim 4, wherein for both storage cylinders the distance of the axis of the stud from the inner cylinder wall is equal.

6. Dual dispenser cartridge assembly as defined in claim 4, wherein the stud of at least one of the two storage cylinders is arranged eccentrically with respect to the cylinder axis.

7. Dual dispenser cartridge assembly as defined in claim 1, wherein the two storage cylinders define an integral unit.

8. Dual dispenser cartridge assembly as defined in claim 7, wherein the two storage cylinders are interlocked near their rear and front ends by means of connecting webs.

9. Dual dispenser cartridge assembly as defined in claim 1, wherein the two storage cylinders are separately manufactured and are interlocked, at least near their rear ends, by means of one of a plug-in and snap-lock connection.

10. Dual dispenser cartridge assembly as defined in claim 9, wherein there is provided, preferably to the front ends of the two storage cylinders, a locking means to prevent respective longitudinal displacement thereof.

11. Dual dispenser cartridge assembly as defined in claim 1, wherein each of the two discharge channels is defined by two mutually overlapping longitudinal sections which are offset with respect to each other in an axially parallel arrangement.

12. Dual dispenser cartridge assembly as defined in claim 1, wherein the exit cross sections of the two discharge channels, within the transition member, are dimensioned in proportion to the cross section ratio of the two storage cylinders.

13. A cartridge assembly as in claim 1, wherein said means for rendering includes a permanent axial push fit connection between said cylinders and said transition member.

14. Dual dispenser cartridge assembly as defined in claim 1, wherein the discharge openings of the cylinders are arranged symmetrically with respect to the axes of the mounting, the latter having a circular cross-section.

15. A series of dual dispenser cartridge assemblies for two-component compounds, each assembly, comprising:
   two interlocked storage cylinders, separated by double walls, arranged axially parallel side-by-side, and each cylinder having one front end discharge opening, wherein both discharge openings are located next to each other centered on a common diametral plane through both storage cylinders, the distance between the axes of the discharge openings being less than the distance between the cylinder axes, said dual dispensing cartridge assembly being subject to long term storage and subsequent dispensing of said components;
   a transition member positioned ahead of the front end of the storage cylinders, said transition member having for both components a mounting for attachment of a mixer tube, and two discharge channels, extending separately to the extremity of the mounting, said transition member being undetachably integral with both storage cylinders and connecting both said discharge channels to said discharge openings of the storage cylinders, said transition member defining a rigid unit in conjunction with both said storage cylinders;
   means for rendering said transition member undetechably integral with said cylinders;
   each said assembly being of equally rated total volume, however, with variable ratios between the cross-sections of the cylinder pairs, wherein the distance between the cylinder axes for all the cylinder pairs of the series is equal.

16. A series as defined in claim 15, wherein the distance between the axes of the front end discharge openings is equal for all pairs of cylinders within the series.

* * * * *

UNITED STATES PATENT AND TRADEMARK OFFICE
CERTIFICATE OF CORRECTION

PATENT NO. : 4,981,241
DATED : January 1, 1991
INVENTOR(S) : WILHELM A. KELLER

It is certified that error appears in the above-identified patent and that said Letters Patent is hereby corrected as shown below:

On the title page at [76], the Inventor is:

Wilhelm A. Keller
    Grundstrasse 12
    CH-6343 Rotkreuz
    Switzerland.

Signed and Sealed this

Eighth Day of September, 1992

Attest:

DOUGLAS B. COMER

*Attesting Officer*      *Acting Commissioner of Patents and Trademarks*